United States Patent [19]

Remz et al.

[11] Patent Number: 5,294,435
[45] Date of Patent: Mar. 15, 1994

[54] STABILIZATION OF EMULSION ADDITIVES TO NAIL POLISH REMOVERS

[75] Inventors: Harvey Remz, Huntington; John Cunningham, Madison; John Russo, Westport; John Wooster, Stratford, all of Conn.

[73] Assignee: Chesebrough-Pond's USA Co. Division of Conopco, Inc., Greenwich, Conn.

[21] Appl. No.: 945,428

[22] Filed: Sep. 14, 1992

Related U.S. Application Data

[63] Continuation of Ser. No. 370,493, Jun. 23, 1989, abandoned.

[51] Int. Cl.$^5$ ................................. A61K 7/04
[52] U.S. Cl. .................... 424/61; 424/78.37
[58] Field of Search ............ 424/61, 81, 78.37

[56] References Cited

U.S. PATENT DOCUMENTS

| | | | |
|---|---|---|---|
| 2,268,642 | 1/1942 | Carter | 424/61 |
| 2,798,053 | 7/1957 | Brown | 260/2.2 |
| 4,032,464 | 6/1977 | Maussner | 252/89 R |
| 4,485,037 | 11/1984 | Curtis | 424/61 |
| 4,530,726 | 7/1985 | Montiel | 424/61 |
| 4,804,486 | 2/1987 | Day | 424/61 |

FOREIGN PATENT DOCUMENTS 009691 4/1980 European Pat. Off. .

OTHER PUBLICATIONS

Publication from Morton Thiokol, Inc., Morton Chemical Division, entitled Polymer Emulsions, Lytron 614 Latex (Chemical Specialties/Technical Infor.).

Publication from Morton Thiokol, Inc., Morton Chemical Division, entitled Polymer Emulsions, Lytron Latex 621 (Chemical Specialties/Technical Infor.).

*Primary Examiner*—Thurman K. Page
*Assistant Examiner*—Peter F. Kulkosky
*Attorney, Agent, or Firm*—Milton L. Honig

[57] ABSTRACT

A nail polish or lacquer removing composition is reported which includes a volatile organic solvent such as acetone, a conditioning agent which is a $C_8$–$C_{20}$ fatty acid or salt thereof, and a suspending polymer which is a styrene/(meth)acrylic copolymer. Absent the suspending copolymer, the conditioning agent tends to separate from the formulation.

6 Claims, No Drawings

STABILIZATION OF EMULSION ADDITIVES TO NAIL POLISH REMOVERS

This is a continuation application of Ser. No. 07/370,493 filed Jun. 23, 1989, now abandoned.

BACKGROUND OF THE INVENTION

1. Field of the Invention

The invention relates to stabilization of a lotion or cream added to a nail polish remover.

2. The Related Art

Products have long been marketed for the removal of nail polish (lacquer) from fingernails and toenails. Essentially, these products contain only a solvent(s) with which to dissolve the lacquer. Typically, the solvent will be a relatively volatile material such as acetone or ethyl acetate.

Organic solvents have a tendency to remove natural oils/fats found in the skin. Nail polish is usually removed by applying the stripping product to a cotton ball and rubbing the nail. Too often surrounding skin also comes in contact with the solvent laden cotton ball. As a result, this contacted skin is defatted. To overcome the defatting phenomenon, it would be desirable to include ingredients within the nail polish remover that would counteract the stripping of oils/fats from the skin. One approach has been to incorporate emollients or other beneficial agents along with the solvent which are depositable so as to either replace or form a barrier for retaining the body's natural oils.

Although not specifically directed to this problem, there have been reports of nail polish removers with additional nail benefit ingredients. For instance, U.S. Pat. No. 4,032,464 (Mausner) discloses a composition not only containing nail lacquer solvent but also incorporating an aqueous solution of a chelating agent, a humectant, a proteinaceous material and vitamins A and D. These ingredients are dispersed in an acetone vehicle thickened with Carbopol to form a homogeneous creamy stable mixture.

EP-A-0 009 691 (Mullin et al.) reports a lacquer remover preparation held within and applied from a foam. Among the advantages of the foam form is the ready incorporation of other chemicals that would normally not be compatible with typical nail remover solvents. Lathering agents are said to be includable such as stearic acid, soaps and the like. Conditioners and emollients may also be incorporated such as glycerine, lanolin, mineral oil, fatty esters, glycols and carboxyvinyl polymer resins partially neutralized by triethanolamine (e.g. TEA Carbopol 941). Stability problems normally associated with liquid products have been avoided by incorporating all the ingredients within a foamed solid. On the other hand, there are disadvantages with foams. Unlike the small bottles of liquid nail remover, foam products require large containers that are not easily portable within a woman's handbag. Another problem is that upon storage there may occur separation of the liquid components within the foam pockets.

Accordingly, it is an object of the present invention to provide a nail polish (lacquer) remover containing ingredients additional to that of solvent which ameliorate the problem of defatting and deliver conditioning oils to the skin.

A further object of the present invention is to provide a nail polish (lacquer) remover that additionally contains skin conditioning agents in the form of a physically stable emulsion.

These and other objects of the present invention will become more apparent through the detailed description of the invention that follows hereinafter.

SUMMARY OF THE INVENTION

A polish-lacquer removing composition is provided comprising:

(i) from about 70% to about 99.5% of volatile organic solvent;

(ii) from about 0.01% to about 5% of a conditioning agent selected from $C_8$–$C_{20}$ fatty acid and salts thereof; and (iii) from about 0.1% to about 7% of a suspending polymer which is a styrene/(meth)acrylic copolymer.

DETAILED DESCRIPTION OF THE INVENTION

The present invention provides compositions that include a major amount of a volatile organic solvent in combination with skin conditioning agents. These agents are not normally either soluble or stably dispersible within the solvent system. Now it has been discovered that conditioning agents may be stably suspended with the aid of a certain type polymer.

Suspending polymers suitable for the present invention are those of the styrene/(meth)acrylic copolymer variety. These copolymers may optionally be cross-linked with such agents as divinylbenzene. Specific examples are styrene/acrylate copolymer (Lytron 614 and 621), styrene/acrylate/divinylbenzene copolymer (Lytron 284, 288 and 295), and styrene/PEG-10 maleate/nonoxynol-10 maleate/acrylate copolymer (Lytron 305). Most preferred are the type of copolymers exemplified by Lytron 295 and 621, the latter being especially preferred. Suspending polymer will normally be present in an amount from about 0.1% to about 7% by weight of the total composition. Preferably, the amount will range from about 0.5% to about 5%, optimally about 1% by weight.

Volatile organic solvents employed for the present invention will have a boiling point lower than 100° C., preferably below 50° C. Acetone and ethyl acetate are the solvents of choice. These may, however, be utilized in combination with other solvents such as methyl ethyl ketone. Amount of the solvent will range from about 70% to about 99.5% by weight of the total composition. Preferably, the amount will range from about 78 to about 88%, optimally, about 80% by weight.

Water may also be present in the compositions. Amounts of water may range anywhere from a trace up to about 25%, preferably from about 8% to about 15%, optimally between about 10% and 13% by weight.

Of course, a key feature of the composition is the presence of a conditioning agent. This agent is defined herein as a $C_8$–$C_{20}$ fatty acid or salt thereof. Typical fatty acids include lauric, myristic, oleic, stearic acids and mixtures thereof; preferably the acid or salt is based upon stearic acid. Typical fatty acid salts are those with cations such as sodium, potassium, diethanolammonium, triethanolammonium, ammonium ions and mixtures thereof. Conditioning agents will be present in an amount from about 0.01% to about 5%, preferably from about 0.05% to about 1% by weight of the total composition.

Optionally, there may be included within the compositions of the invention humectants such as glycerine, propylene glycol, sorbitol and mixtures thereof. Amounts of these components may range from about 0.1% to about 10% by weight of the total composition.

Emollients such as fatty acid esters (e.g. glycol and diglycol stearate, glycerol stearate, cetyl acetate), mineral oil, silicone oil, lanolin and lanolin derivatives may be present in amounts from about 0.01% to about 3% by weight of the total composition.

Conditioning agent, emollient and other oily materials are normally first prepared as an oil-in-water emulsion. This emulsion is then incorporated into the volatile organic solvent. Typical amount of the emulsion may range from about 1% to about 10% of the total composition.

The following Examples will more fully illustrate the embodiments of this invention. All parts, percentages and proportions referred to herein and in the appended claims are by weight of the total composition unless otherwise stated.

EXAMPLE 1

A composition typical of the present invention is outlined in Table I.

TABLE I

| Ingredient | Weight % |
| --- | --- |
| Acetone | 75-85 |
| Water | 10-15 |
| Glycerine | 1-8 |
| Lytron 621 | 0.5-2 |
| Fragrance and Color | 0.5-2 |
| Mineral Oil | 0.01-0.5 |
| Carbopol 934 (2% dispersion) | 0.01-0.5 |
| Propylene Glycol | 0.01-0.5 |
| Stearic Acid | 0.01-0.5 |
| Glycol Stearate | 0.01-0.5 |
| Cetyl Acetate | 0.01-0.3 |
| Triethanolamine | 0.01-0.3 |
| Glycerol Stearate | 0.01-0.2 |
| Cetyl Alcohol | 0.01-0.1 |
| Methyl Paraben, Propyl Paraben and Disodium EDTA | 0.01-0.1 |
| Magnesium Aluminum Silicate (Veegum) | 0.01-0.05 |
| Silicone Fluid | 0.01-0.05 |

EXAMPLE 2

Absent the presence of Lytron 621 as a suspending agent, the formula of Table I exhibited precipitation of white particles. Solubility tests were conducted to investigate which of the various non-solvent components was incompatible with the formulation. A test solution was prepared from 89.9% acetone, 10% water and 0.1% additive. Table II lists the results of solubility tests on the various additives.

TABLE II

| Additive Compatibility | |
| --- | --- |
| Additive | Precipitate Formation |
| Stearic Acid | Severe |
| Veegum | Moderate |
| Silicone Fluid | Slight |
| Glycerine | Slight |
| Mineral Oil | None |
| Cetyl Alcohol | None |
| Glycol Stearate | None |
| Glycerol Stearate | None |
| Triethanolamine | None |
| Carbopol 934 | None |

From the above Table, it is evident that the major insoluble component is that of stearic acid.

EXAMPLE 3

Suspending performance of various polymers was investigated. The formula outlined in Table I was employed with the exception that the type of Lytron was varied.

TABLE III

| Effect of Various Lytron Polymers | | |
| --- | --- | --- |
| Polymer | | Precipitate |
| Chemical Identity | Trademark | Formation |
| Styrene/Acrylate copolymer | Lytron 621 | Trace |
| Styrene/Acrylate/divinylbenzene copolymer | Lytron 295 | Very slight |
| Styrene/Acrylate Copolymer | Lytron 614 | Slight-Moderate |
| Styrene/PEG-10 Maleate/Nonoxynol-10 Maleate/Acrylate Copolymer | Lytron 305 | Moderate |
| Styrene/Acrylamide Copolymer | Lytron 308 | Severe |
| Styrene/Acrylate/PEG-10 Dimaleate Copolymer | Lytron 300 | Phase Separation |

The Lytron materials were all obtained from the Morton Chemical Division of Morton-Thiokol Corporation, of Chicago, Ill. From Table III, it is evident Lytron 621 provided the best suspending activity. Lytron 295, a cross-linked material, was somewhat less effective. Unacceptable suspending properties were noted for the Lytron 305, 308 and 300 materials.

EXAMPLE 4

Illustrated in this Example is the effect of altering the level of the suspending polymer. Lytron 295 was substituted for Lytron 621 at various levels in the formulation outlined under Table I. Results are reported in Table IV.

TABLE IV

| Polymer Concentration Effects | |
| --- | --- |
| Level of Suspending Polymer (Percentage) | Precipitate Formation |
| 0.5 | Some separation |
| 1.0 | Very slight separation |
| 1.5 | Trace separation |
| 2.0 | No separation |
| 2.5 | No separation |
| 10.0 | Separation |

From the results, it is evident that there is an effective range for the suspending polymer of between 0.5% to upwards of 2.5% but less than 10% by weight.

The foregoing description and Examples illustrate selected embodiments of the present invention and in light thereof various modifications will be suggested to one skilled in the art, all of which are in the spirit and purview of this invention.

What is claimed is:

1. A polish-lacquer removing composition comprising:
   (i) from about 70% to about 99.5% of volatile organic solvent which is acetone, the remainder of the solvent being water;
   (ii) from about 0.01% to about 5% of a conditioning agent selected from the group consisting of stearic acid, sodium stearate, triethanolamine stearate and mixtures thereof; and
   (iii) from about 0.2% to about 7% of a suspending polymer which is a styrene/(meth)acrylic copolymer selected from the group consisting of non-crosslinked styrene/(meth)acrylate and styrene/-(meth)acrylate divinylbenzene copolymers;

and wherein any precipitate formation in said composition is reduced or avoided.

2. A composition according to claim 1 wherein water is present in an amount from about 8% to about 13% by weight.

3. A composition according to claim 1 wherein the suspending polymer is present in an amount from about 0.5% to about 2.5% by weight.

4. A composition according to claim 1 wherein acetone is present in an amount from about 75% to about 85% by weight.

5. A composition according to claim 1 further comprising from about 0.1 to about 10% of a humectant selected from the group consisting of glycerine, propylene, glycol, sorbitol and mixtures thereof.

6. A composition according to claim 1 wherein said suspending agent is non-crosslinked styrene/acrylate copolymer.

* * * * *